(12) United States Patent
Choi et al.

(10) Patent No.: US 12,290,699 B2
(45) Date of Patent: May 6, 2025

(54) LIGHT OUTPUTTING DEVICE FOR SCALP CARE, AND CONTROL METHOD THEREFOR

(71) Applicant: LG ELECTRONICS INC., Seoul (KR)

(72) Inventors: Kyuhyoung Choi, Seoul (KR); Kyounghee Kim, Seoul (KR); Hoseong Song, Seoul (KR); Dongwon Kim, Seoul (KR); Gungil Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 644 days.

(21) Appl. No.: 17/625,509

(22) PCT Filed: Jul. 17, 2020

(86) PCT No.: PCT/KR2020/009480
§ 371 (c)(1),
(2) Date: Jun. 21, 2022

(87) PCT Pub. No.: WO2021/010801
PCT Pub. Date: Jan. 21, 2021

(65) Prior Publication Data
US 2023/0181925 A1    Jun. 15, 2023

(30) Foreign Application Priority Data
Jul. 18, 2019    (KR) .................. 10-2019-0087254

(51) Int. Cl.
*A61N 5/06*    (2006.01)
*A61B 5/00*    (2006.01)
(Continued)

(52) U.S. Cl.
CPC .......... *A61N 5/0616* (2013.01); *A61B 5/0013* (2013.01); *A61B 5/0077* (2013.01);
(Continued)

(58) Field of Classification Search
CPC ............................. A61N 5/0616; A61N 5/067
(Continued)

(56) References Cited

U.S. PATENT DOCUMENTS

2015/0127072 A1    5/2015  Pomar
2017/0028216 A1*   2/2017  Medendorp, Jr. .... A61N 5/0616
(Continued)

FOREIGN PATENT DOCUMENTS

DE    102017211782    1/2019
JP    2004136019      5/2004
(Continued)

OTHER PUBLICATIONS

European Patent Office Application Serial No. 20840777.5, Search Report dated Jun. 23, 2023, 6 pages.
PCT International Application No. PCT/KR2020/009480, International Search Report dated Oct. 26, 2020, 4 pages.

*Primary Examiner* — Nadia A Mahmood
(74) *Attorney, Agent, or Firm* — LEE, HONG, DEGERMAN, KANG & WAIMEY

(57) ABSTRACT

A light outputting device for scalp care according to an embodiment of the present invention comprises: a dome-shaped outer case forming the outer shape; an inner case formed inside the outer case; a plurality of laser light sources disposed in the space between the outer case and the inner case; photodiodes included in the plurality of laser light sources, respectively; and a processor which acquires a light amount sensing value of a first photodiode among the plurality of photodiodes, sets an amount of light for a first laser light source including the first photodiode on the basis of the acquired light amount sensing value, and drives the first laser light source on the basis of the set amount of the light.

17 Claims, 14 Drawing Sheets

(51) Int. Cl.
*A61B 5/01* (2006.01)
*A61N 5/067* (2006.01)

(52) U.S. Cl.
CPC ............... *A61B 5/01* (2013.01); *A61B 5/448* (2013.01); *A61N 5/067* (2021.08); *A61B 2562/0271* (2013.01); *A61B 2562/029* (2013.01); *A61N 2005/0626* (2013.01); *A61N 2005/0647* (2013.01); *A61N 2005/0652* (2013.01)

(58) Field of Classification Search
USPC .......................................................... 607/89
See application file for complete search history.

(56) References Cited

U.S. PATENT DOCUMENTS

| | | |
|---|---|---|
| 2020/0221994 A1 | 7/2020 | Kumpan-Bahrami |
| 2022/0001195 A1 | 1/2022 | Lim et al. |

FOREIGN PATENT DOCUMENTS

| | | | |
|---|---|---|---|
| JP | 2004136019 A | * | 5/2004 |
| JP | 201119706 | | 2/2011 |
| KR | 20150025829 | | 3/2015 |
| KR | 20150025829 A | * | 3/2015 |
| KR | 20150101709 | | 9/2015 |
| WO | 2020080636 | | 4/2020 |

\* cited by examiner

[Fig. 1]
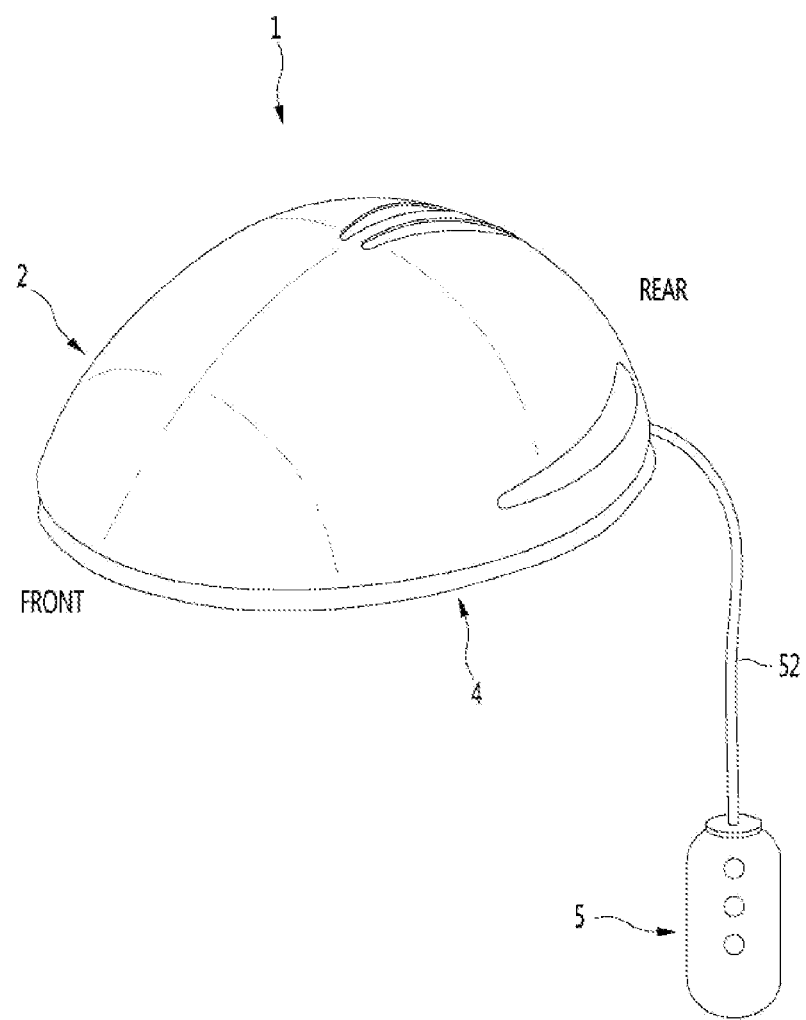

[Fig. 2]
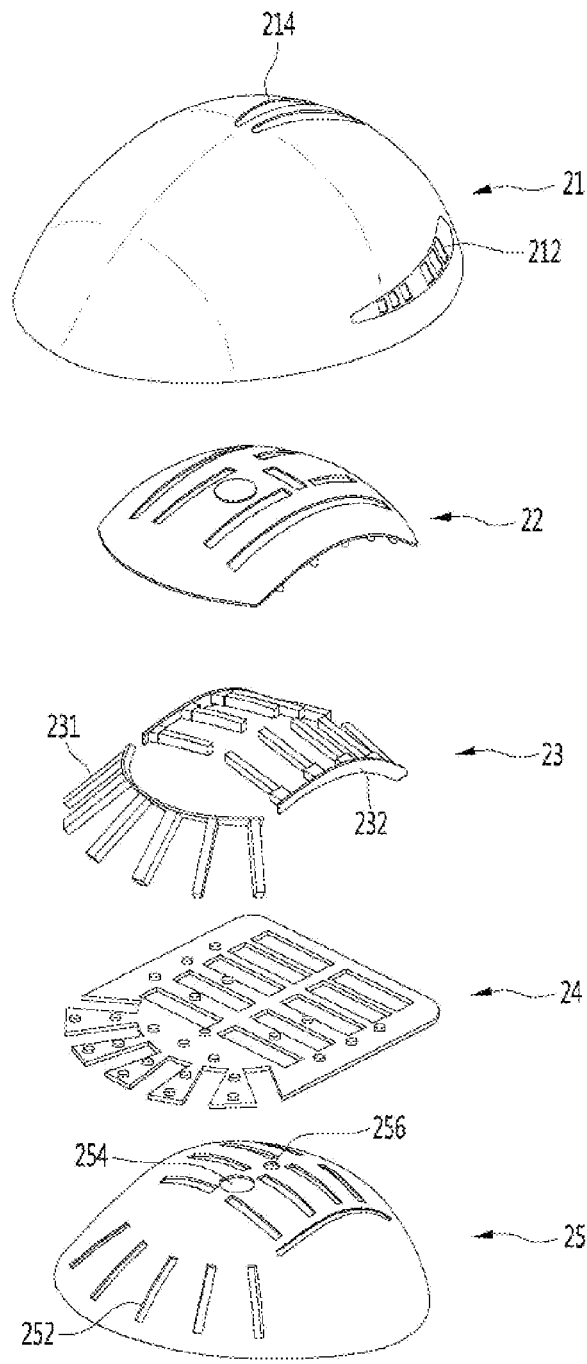

【Fig. 3】
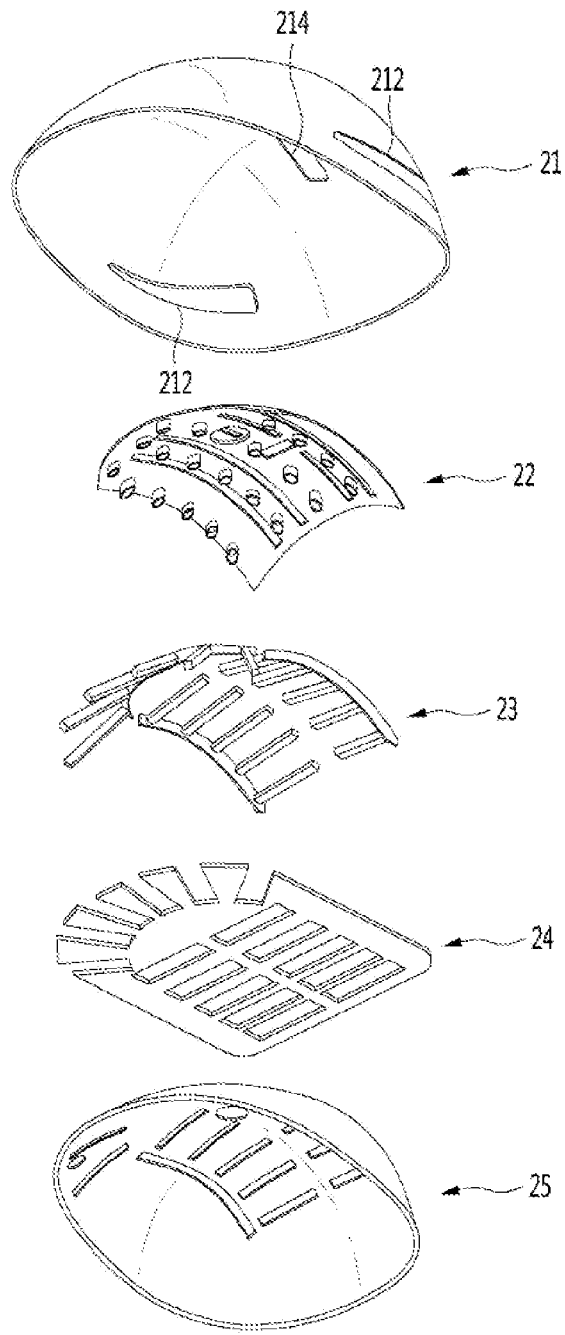

[Fig.4]
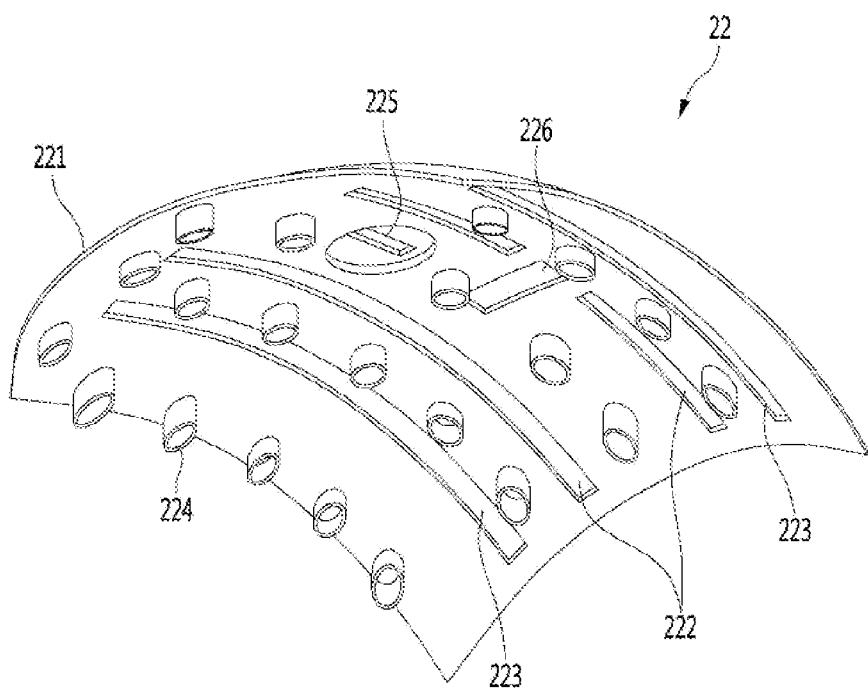

[Fig. 5]
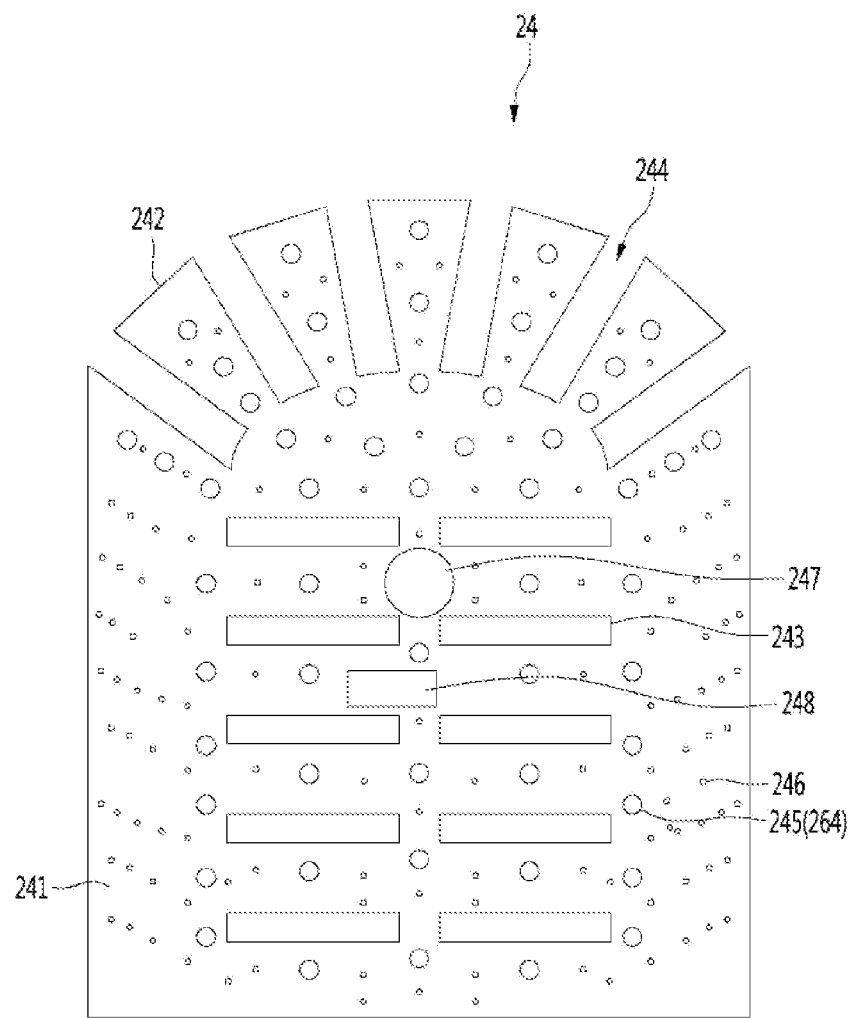

[Fig. 6]
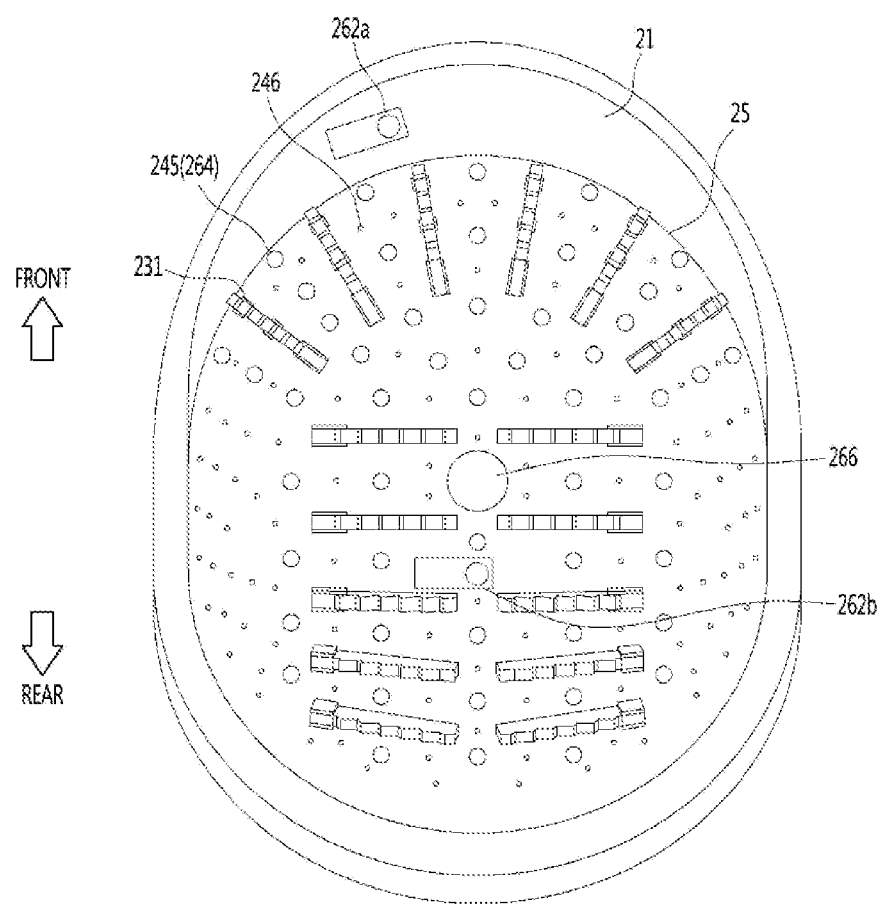

[Fig. 7]
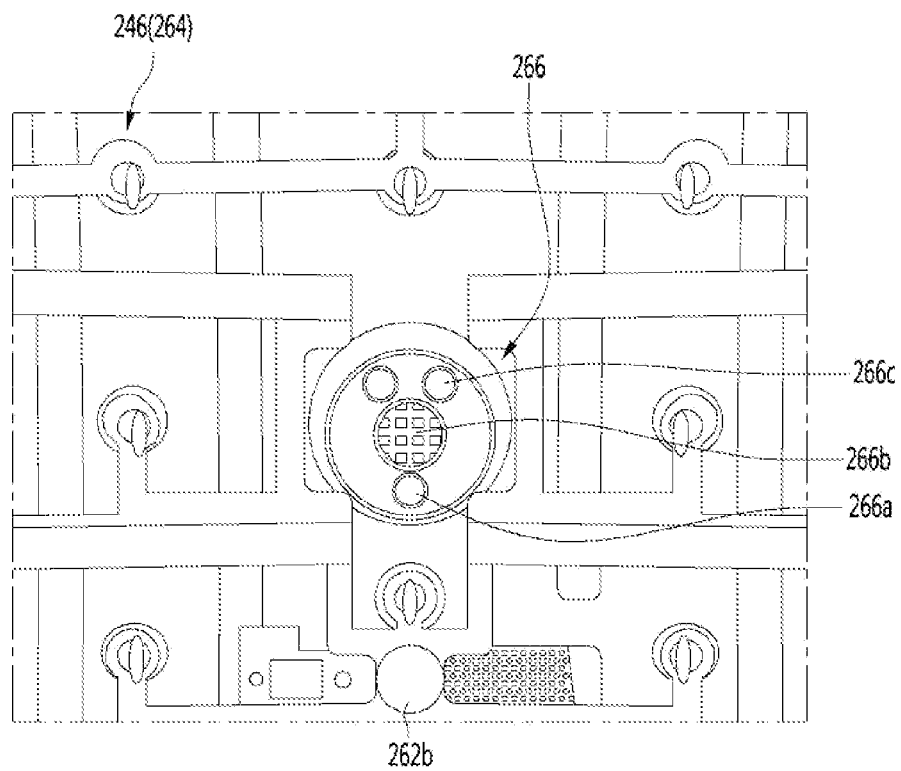

【Fig. 8】
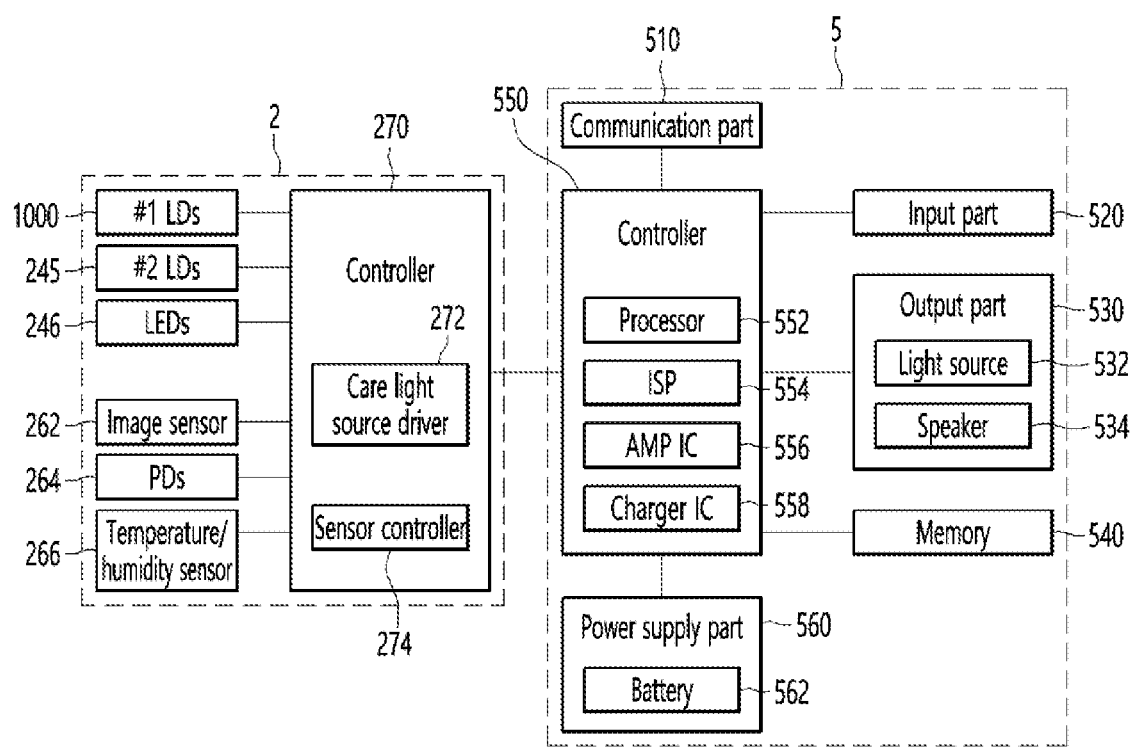

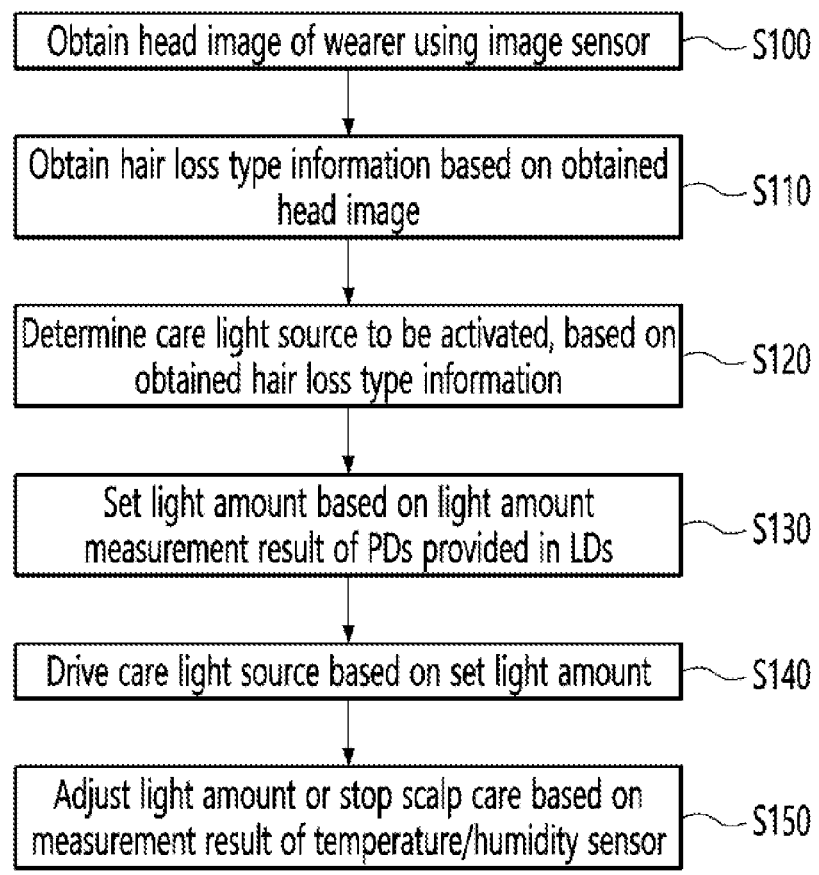
[Fig. 9]

【Fig. 10】
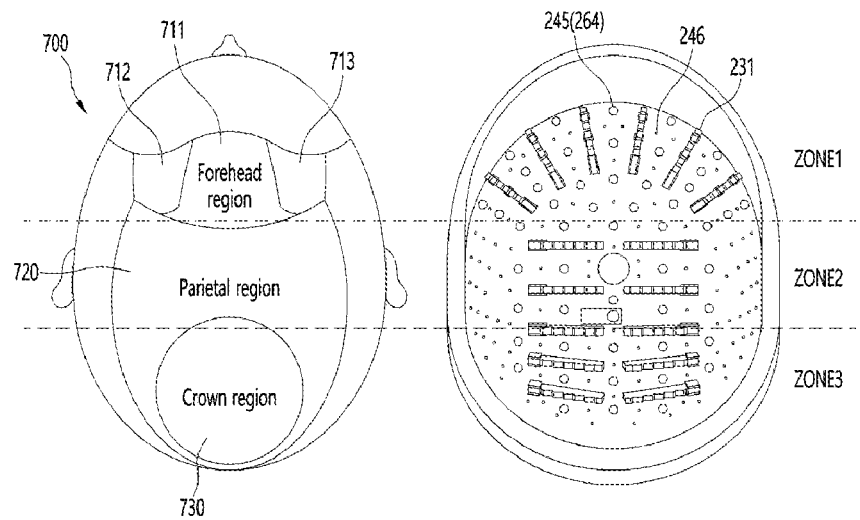
【Fig. 11】
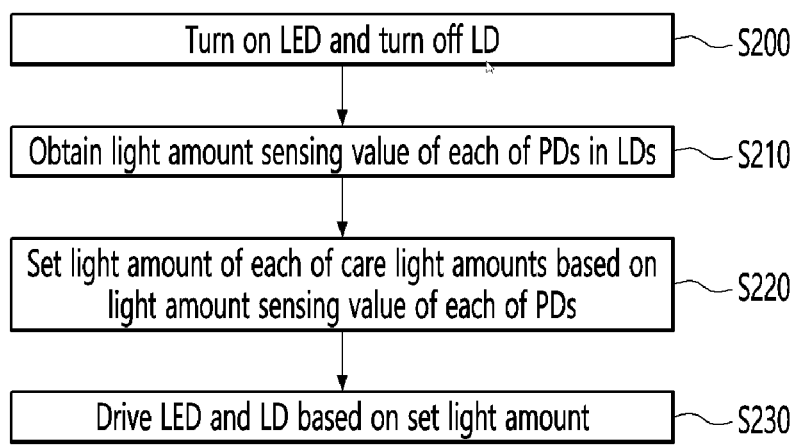

【Fig. 12】
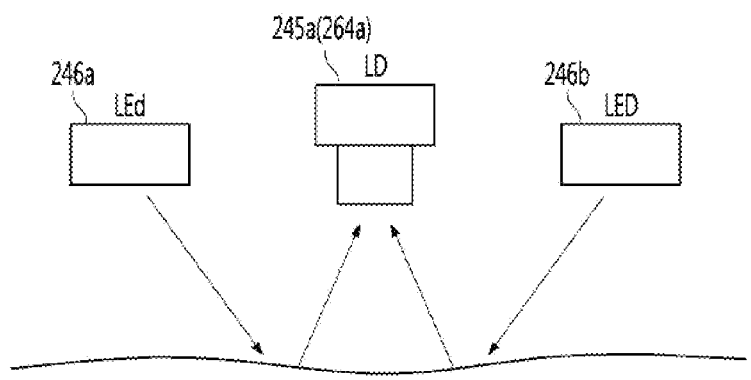
【Fig. 13】
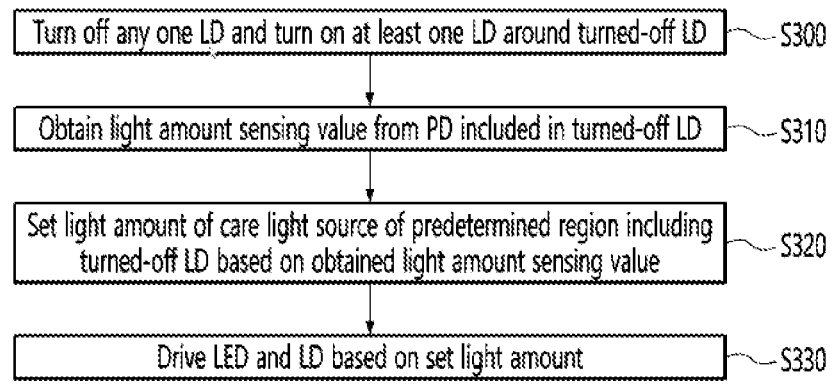

【Fig. 14】
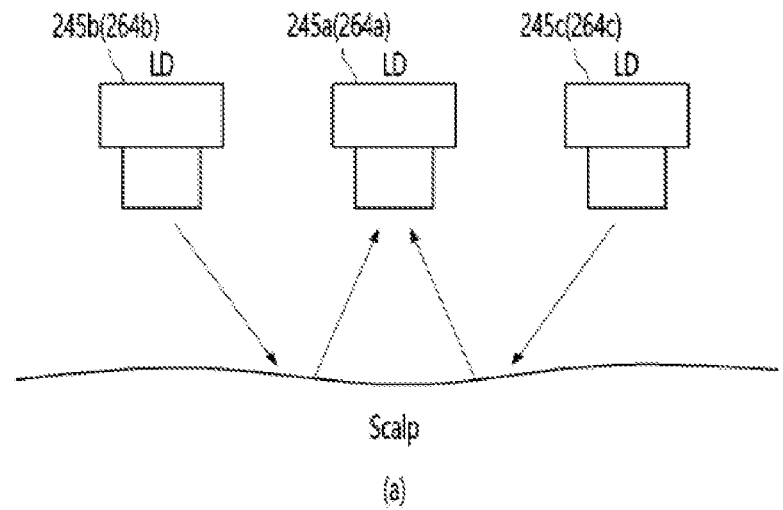
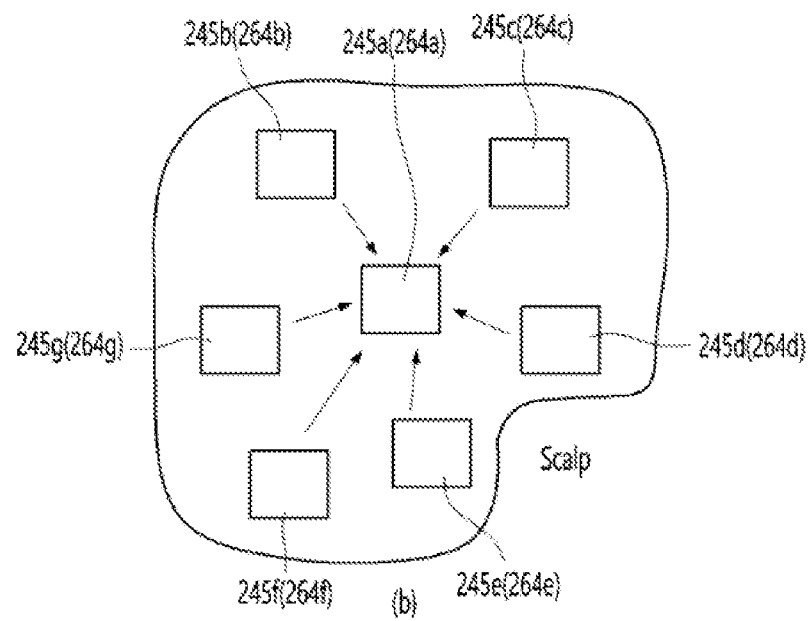

[Fig. 15]
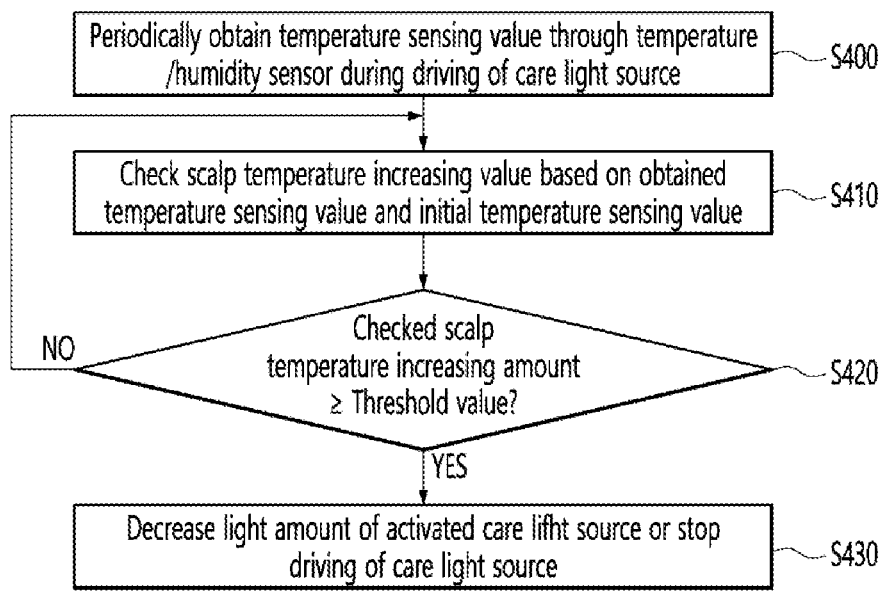

[Fig. 16]
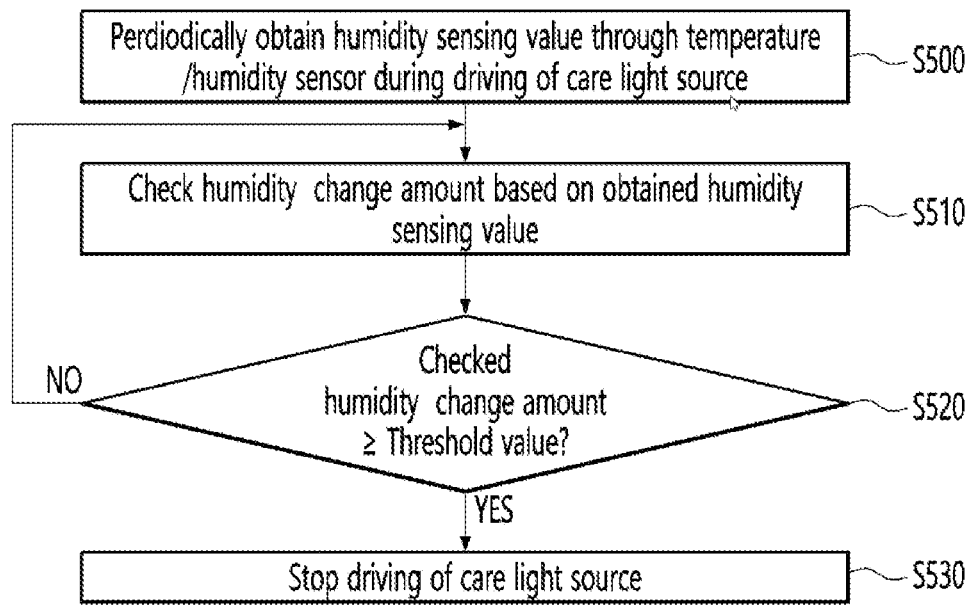

LIGHT OUTPUTTING DEVICE FOR SCALP CARE, AND CONTROL METHOD THEREFOR

CROSS-REFERENCE TO RELATED APPLICATIONS

This application is the National Stage filing under 35 U.S.C. 371 of International Application No. PCT/KR2020/009480, filed on Jul. 17, 2020, which claims the benefit of earlier filing date and right of priority to Korean Application No. 10-2019-0087254, filed on Jul. 18, 2019, the contents of which are all incorporated by reference herein in their entirety.

TECHNICAL FIELD

The present disclosure relates to a light outputting device, and more particularly, to a device that is worn on a user's head and outputs light for scalp care.

BACKGROUND ART

Modern people recognize their appearance as an important factor to inform and express themselves to others, and thus, invest a lot of money and time in appearance management to overcome flaws in appearance.

Among them, hair loss is caused by various causes such as environmental, genetic, mental, and physical, and various techniques and treatments for hair loss prevention or treatment are being studied.

Low level laser therapy (LLLT) is a therapy for irradiating a beam of a specific wavelength to a living tissue, inducing the promotion of metabolism in the corresponding portion, and activating the function of the tissue. Laser light used as a low level laser therapy generates effects such as an increase in capillary production, an increase in blood oxygen concentration, and promotion of collagen production by penetrating into a living tissue and activating ions of cells.

Based on such low level laser therapy, methods or devices for promoting hair growth by irradiating laser light to the scalp to activate hair follicles and biological tissues around the hair follicles have emerged.

DISCLOSURE

Technical Problem

An object of the present disclosure is to provide a light outputting device for scalp care that performs an optimal scalp care operation according to a user's hair loss condition.

Another object to be solved by the present disclosure is to provide a light outputting device for scalp care that can actively control the operation of the care light source according to the user's scalp condition while the care light source is being driven.

Technical Solution

A light outputting device for scalp care according to an embodiment of the present disclosure includes a dome-shaped outer case configured to form an outer appearance, an inner case configured to be formed inside the outer case, a plurality of laser light sources configured to be disposed in a space between the outer case and the inner case, a photodiode configured to be provided in each of the plurality of laser light sources, and a processor configured to obtain a light amount sensing value of a first photodiode among a plurality of photodiodes, based on the obtained light amount sensing value, to set the light amount for the first laser light source including the first photodiode, and to drive the first laser light source based on a set amount of light.

The processor may set the light amount for the first laser light source to a first light amount in a case where the light amount sensing value is a first sensing value, and set the light amount to the first laser light source to a second light amount equal to or greater than the first light amount in a case where the light amount sensing value is a second sensing value higher than the first sensing value.

According to an embodiment, the processor may turn on at least one laser light source disposed within a predetermined distance from the first laser light source among the plurality of laser light sources and obtain the light amount sensing value of a first photodiode based on light emitted when the at least one laser light source is turned on.

According to an embodiment, the processor may sequentially turn on the at least one laser light source and sequentially obtains at least one light amount sensing value through the first photodiode, calculate an average value of at least one sequentially obtained light amount sensing value, and set an amount of light for the first laser light source based on the calculated average value.

The light outputting device for scalp care of claim may further include a plurality of LEDs disposed in the space between the outer case and the inner case, in which the processor may set a light amount for at least one LED within a predetermined distance from the first laser light source based on a light amount sensing value of the first photodiode.

According to an embodiment, the processor may turn on at least one LED among the plurality of LEDs and obtain the light amount sensing value of the first photodiode based on the light emitted when the at least one LED is turned on.

The light outputting device for scalp care may further include a temperature sensor, in which the processor may obtain a temperature sensing value through the temperature sensor while driving at least one of the plurality of laser light sources and adjust the amount of light of the at least one laser light source during the driving or stop the driving of the at least one laser light source based on the obtained temperature sensing value.

According to an embodiment, the processor may check the amount of increase in scalp temperature based on the difference between the initial temperature sensing value and the obtained temperature sensing value and reduce the amount of light from the at least one laser light source in a case where the checked scalp temperature increase amount is higher than a threshold value.

According to an embodiment, the processor may obtain a temperature sensing value through the temperature sensor after a predetermined time has elapsed from the time when the amount of light of the at least one laser light source is reduced, check the amount of increase in scalp temperature based on the difference between the initial temperature sensing value and the obtained temperature sensing value, and stop the driving of the at least one laser light source in a case where the checked scalp temperature increase amount is maintained higher than the threshold value.

The light outputting device for scalp care may further include a humidity sensor, in which the processor periodically may obtain a humidity sensing value through the humidity sensor during the driving of at least one of the plurality of laser light sources and stop the driving of the at least one laser light source during the driving according to a humidity change amount checked based on the periodically obtained humidity sensing value.

The light outputting device for scalp care may further include at least one image sensor disposed to face the inside of the light outputting device for scalp care, in which the processor may obtain a head image including the user's scalp through the at least one image sensor, obtain the user's hair loss type information based on the obtained head image, and select at least one laser light source to be driven among the plurality of laser light sources based on the obtained hair loss type information.

The light outputting device for scalp care may further include a communication part configured to connect with the server or electronic device, in which processor may control the communication part to transmit the obtained head image to the server or the electronic device and receive, from the server or the electronic device, the hair loss type information based on the head image.

A method for controlling a light outputting device for scalp care according to an embodiment of the present disclosure includes a step of obtaining a light amount sensing value of a first photodiode among a plurality of photodiodes, a step of setting an amount of light for a first laser light source including the first photodiode based on the obtained light amount sensing value, and a step of driving the first laser light source based on a set amount of light.

Advantageous Effect

According to an embodiment of the present disclosure, the light outputting device for scalp care may determine the user's hair loss type using an image sensor such as a camera and may adjust the driving of the care light source according to the determined hair loss type.

In addition, the light outputting device may set the light amount differently according to the hair loss progress of each of the scalp regions by using the light amount sensing values of the photodiodes provided in the laser light sources dispersed in various regions in the device.

Accordingly, the light outputting device may provide a more efficient scalp care function by using the user's hair loss type and the hair loss progress for each scalp region.

In addition, the light outputting device may actively adjust the amount of light or drive of the care light source according to the user's scalp condition (temperature, humidity, or the like) while the care light source is driven according to the performance of the scalp care function. Accordingly, deterioration or damage to the performance of the light outputting device may be prevented, and the risk of deterioration of the user's scalp condition may be prevented in advance.

DESCRIPTION OF DRAWINGS

FIG. 1 is a perspective view illustrating a light outputting device for scalp care according to an embodiment of the present disclosure.

FIG. 2 is an exploded perspective view illustrating the care main body of the light outputting device illustrated in FIG. 1 as viewed from above.

FIG. 3 is an exploded perspective view illustrating the care main body of the light outputting device illustrated in FIG. 1 as viewed from below.

FIG. 4 is a view for explaining the support part included in the care main body in more detail.

FIG. 5 is a bottom view illustrating the care light source mounting part included in the care main body.

FIG. 6 is a bottom view illustrating a care main body of the light outputting device illustrated in FIG. 1.

FIG. 7 is an enlarged view illustrating a laser light source, an image sensor, and a temperature/humidity sensor included in the care main body.

FIG. 8 is a block diagram illustrating a control configuration of a light outputting device for scalp care according to an embodiment of the present disclosure.

FIG. 9 is a flowchart illustrating a method for controlling a light outputting device for scalp care according to an embodiment of the present disclosure.

FIG. 10 is an exemplary view related to an operation of determining a care light source to be activated based on the user's hair loss type described in FIG. 9.

FIG. 11 is a flowchart illustrating an embodiment of an operation of setting a light amount of a care light source based on a light amount sensing value of photodiodes included in laser light sources.

FIG. 12 is an exemplary view related to the embodiment of FIG. 11.

FIG. 13 is a flowchart for explaining an embodiment of an operation of setting a light amount of a care light source based on a light amount sensing value of photodiodes included in laser light sources.

FIG. 14 is an exemplary view related to the embodiment of FIG. 13.

FIG. 15 is a flowchart for explaining an operation in which the light outputting device for scalp care adjusts the operation of the care light source according to the temperature change detected through the temperature/humidity sensor while the care light source is being driven.

FIG. 16 is a flowchart for explaining an operation in which the light outputting device for scalp care adjusts the operation of the care light source according to the humidity change detected through the temperature/humidity sensor while the care light source is being driven.

BEST MODE

Hereinafter, the embodiments disclosed in the present specification will be described in detail with reference to the accompanying drawings, but the same or similar components are assigned the same reference numerals regardless of reference numerals, and overlapping descriptions thereof will be omitted. The suffixes "module" and "part" for the components used in the following description are given or mixed in consideration of only the ease of writing the specification, and do not have distinct meanings or roles by themselves. In addition, in describing the embodiments disclosed in the present specification, if it is determined that detailed descriptions of related known technologies may obscure the subject matters of the embodiments disclosed in the present specification, the detailed description thereof will be omitted. In addition, it should be understood that the accompanying drawings are only for easy understanding of the embodiments disclosed in the present specification, and the technical spirit disclosed herein is not limited by the accompanying drawings, and all changes, equivalents, and substitutes included in the spirit and the technical scope of the present disclosure are included.

Terms including an ordinal number, such as first and second, may be used to describe various components, but the components are not limited by the terms. The above terms are used only for the purpose of distinguishing one component from another.

When a component is referred to as being "connected" or "accessed" to another component, it should be understood that the component may be directly connected or accessed to another component, but there may be other components in between. On the other hand, when it is said that a component is "directly connected" or "directly accessed" to another element, it should be understood that there are no other component in between.

The singular expression includes the plural expression unless the context clearly dictates otherwise.

It should be understood that, in the present application, terms such as "comprises" and "have" are intended to designate that a feature, number, step, operation, component, part, or combination thereof described in the specification exists, but this does not preclude the possibility of the existence or addition of one or more other features, numbers, steps, operations, components, parts, or combinations thereof.

Hereinafter, embodiments of the present disclosure will be described in detail with reference to the accompanying drawings in the present specification.

FIG. 1 is a perspective view illustrating a light outputting device for scalp care according to an embodiment of the present disclosure.

Referring to FIG. 1, a light outputting device 1 for scalp care (hereinafter referred to as a 'light outputting device') according to an embodiment of the present disclosure can be implemented to be worn on a user's head portion and output light to the user's scalp. The light outputting device 1 may provide a function of accelerating hair growth by activating hair follicle cells, increasing capillary production, increasing blood oxygen concentration, and promoting collagen production by outputting the light.

This light outputting device 1 may include a care main body 2, a circumference adjustment part 4, and an operation device 5.

The care main body 2 is formed in a kind of dome shape to correspond to the shape of a person's head, so that light can be evenly irradiated to the user's scalp.

According to an embodiment, the care main body 2 may have a front curvature higher than a rear curvature when viewed from the upper portion in terms of similarity to a human head shape, but this is not necessarily the case.

In other words, in the present specification, the term "dome" is a concept including not only a geometric dome itself, but also a shape similar to a dome. In the present specification, a dome-like shape may mean a shape having an arcuate (or streamlined) shape in each of the left and right direction and the front and rear direction.

The care main body 2 may be provided with a plurality of light sources for outputting light for user's scalp care. The plurality of light sources may include laser light sources (eg, laser diodes) that output laser light and LEDs. For example, the plurality of light sources may emit red light having a wavelength of about 630 nm to 670 nm, but is not limited thereto, and may emit red light or infrared light. Red light can promote hair growth through the activation of hair follicle cells.

Meanwhile, the intensity of the laser light emitted by the laser light source is stronger than the light emitted from the LED, and the laser light can penetrate more deeply into the skin, thereby providing a higher scalp care effect. Accordingly, the laser light source in the care main body 2 is disposed to irradiate the laser light to a region where the need for scalp care is higher when worn by the user, thereby enabling intensive care for the region. The care light source provided in the care main body 2 will be described in more detail later with reference to the drawings.

Meanwhile, the care main body 2 may further include various sensors such as a sensor for measuring the user's scalp condition (temperature, humidity, or the like), at least one sensor for detecting the user's hair loss type, and a sensor for detecting whether a light outputting device is worn.

The circumference adjustment part 4 may be formed at the lower end of the care main body 2 and may come into contact with the side circumferential surface of the head when worn by the user. The circumference adjustment part 4 may include a structure capable of adjusting the length to correspond to the side circumferential surface of the head of various users. The care main body 2 may be stably worn on the user's head by the circumference adjustment part 4 to irradiate light to the scalp.

Meanwhile, the light outputting device 1 may further include a user manipulation device 5 connected to the care main body 2. For example, the user manipulation device 5 may be connected to the care main body 2 by wire through a cable 52 or the like, but this is not always the case and may be connected wirelessly through a wireless communication method.

For example, the user manipulation device 5 may be formed in a cylindrical shape to be easily held and used by a user. The user manipulation device 5 may include at least one button as an input part for manipulating the light outputting device 1.

The user manipulation device 5 may provide an interface for turning on/off the power of the care main body 2 or setting an operation mode of the care main body 2 from the user. As the user manipulation device 5 is implemented as a configuration separate from the care main body 2, the user can conveniently adjust the operation of the care main body 2 by using the user manipulation device 5 even while wearing the care body 2.

In addition, the user manipulation device 5 may be provided with a battery that provides power for the operation of the light outputting device. As the battery is provided in the user manipulation device 5, the weight of the care main body 2 can be minimized to minimize user discomfort. Control components included in the user manipulation device 5 will be described later with reference to FIG. 13.

Hereinafter, embodiments related to the structure of the care main body 2 and the arrangement of light sources will be described in more detail with reference to FIGS. 2 to 7.

FIG. 2 is an exploded perspective view illustrating the care main body of the light outputting device illustrated in FIG. 1 as viewed from above. FIG. 3 is an exploded perspective view illustrating the care main body of the light outputting device illustrated in FIG. 1 as viewed from below. FIG. 4 is a view for explaining the support part included in the care main body in more detail. FIG. 5 is a bottom view illustrating the care light source mounting part included in the care main body.

Referring to FIGS. 2 to 3, the care main body 2 may include an outer case 21, a support part 22, a light guide part 23, a care light source mounting part 24, and an inner case 25.

The outer case 21 may form the overall outer appearance of the care main body 2. For example, the outer case 21 may be made of a material such as plastic, stainless use steel (SUS), or the like, to protect the components inside the care main body 2 from the outside. Meanwhile, the outer case 21 is formed to be opaque, it is possible to block the light emitted from the laser light sources or LEDs disposed therein from being irradiated to the outside.

According to an embodiment, a side opening 212 and/or an upper opening 214 may be formed in the outer case 21. When the care main body 2 is worn, air can circulate between the inner portion of the care main body 2 (the space between the care main body 2 and the head) and the outer portion of the care main body 2 through the lateral opening 212 and/or the upper opening 214. Accordingly, heat generated according to the driving of the care light sources of the care main body 2 is effectively released to the outside, thereby preventing deterioration of the performance of the light source.

Referring to FIGS. 2 to 4, the support part 22 may be provided on the lower side of the outer case 21.

The support part main body 221 forming the overall outer shape of the support part 22 may be formed in an arcuate shape in each of the left and right direction and the front and rear direction corresponding to the shape of the outer case 21.

The support part 22 may be fastened to the inner surface of the outer case 21, but this is not necessarily the case. For example, in a case where the support part 22 is implemented to be fastened to the inner surface of the outer case 21, at least one fastening groove 222 may be formed in the support part main body 221, and at least one fastening protrusion corresponding to at least one fastening groove 222 may be formed on the inner surface of the outer case 21. Meanwhile, at least one fastening groove 222 may function as an opening that enables air circulation between the inside and the outside of the care main body 2.

Meanwhile, the support part 22 may support and fix the light guide part 23 and the care light source mounting part 24 with respect to the outer case 21 and/or the inner case 25.

Referring to FIG. 4, at least one light guide fastening groove 223 may be formed in the support part main body 221. For example, the at least one light guide part fastening groove 223 may be formed in the form of an opening in a portion of the support part main body 221. Since the laser light source mounting part 232 of the light guide part 23 is inserted into the light guide part fastening groove 223, the light guide part 23 may be supported and fixed by the support part 22.

In addition, a plurality of PCB fixing parts 224 may be formed on the lower surface of the support part main body 221.

For example, each of the plurality of PCB fixing parts 224 may form an accommodation space in which a plurality of insertion protrusions formed on the upper surface of the care light source mounting part 24 are inserted and accommodated. In a case where the plurality of insertion protrusions are formed in a circular or cylindrical shape, the PCB fixing part 224 may be implemented as a circular ring-shaped protrusion as illustrated in FIG. 4. In this case, the outer diameter of the plurality of insertion protrusions is formed to be equal to or smaller than the inner diameter of the PCB fixing part 224, so that the plurality of insertion protrusions may be accommodated and fixed in the accommodation space. The above embodiment is for convenience of explanation, the shape of the plurality of PCB fixing parts 224 is not limited thereto, and the plurality of PCB fixing parts 224 can be implemented in the various form for fixing and supporting the care light source mounting part 24.

According to an embodiment, a temperature/humidity sensor fixing part 225 and an image sensor fixing part 226 may be further formed on the support part main body 221. The temperature/humidity sensor fixing part 225 may be formed to correspond to an upper portion of the temperature/humidity sensor mounted on the care light source mounting part 24 to fix and support the temperature/humidity sensor. The image sensor fixing part 226 may be implemented as an opening through which an upper portion of the image sensor mounted on the care light source mounting part 24 is fixed and supported.

In other words, by the PCB fixing part 224, the temperature/humidity sensor fixing part 225, and the image sensor fixing part 226, the care light source mounting part 24 may be fixed and supported by the support part 22. Meanwhile, according to an embodiment, the support part 22 may be provided with a fastening part that is directly fastened to the care light source mounting part 24 to fix and support the care light source mounting part 24.

With continued reference to FIGS. 2 and 3, the light guide part 23 and the care light source mounting part 24 may be provided between the support part 22 and the inner case 25.

The light guide part 23 may include a plurality of light guide mechanisms 231 and a laser light source mounting part 232 provided with a first laser light source corresponding to each of the plurality of light guide mechanisms 231.

Each of the plurality of light guide mechanisms 231 may distribute and irradiate laser light emitted from a corresponding first laser light source to a plurality of regions. The first laser light source may be disposed so as not to directly irradiate the laser light in the direction of the user's head (or the direction of the inner case).

The light guide mechanism 231 may be formed in a rod shape, and the first laser light source may emit laser light in the longitudinal direction of the light guide mechanism 231.

In particular, the light guide mechanism 231 may be disposed at an angle closer to the tangent than to the perpendicular to the tangent at a position corresponding to the inner case 25 in the longitudinal direction. For example, the light guide mechanism 231 may be disposed so that the longitudinal direction thereof is parallel to the tangent line, but this is not necessarily the case.

The light guide mechanism 231 may reflect the laser light emitted from the first laser light source and irradiate the laser light in the direction of the user's head (or the direction of the inner case).

Specific details of the light guide mechanism 231 will be described in more detail later with reference to FIGS. 8 to 12.

The laser light source mounting part 232 may include a plurality of PCBs on which at least one first laser light source is mounted, respectively. Although the laser light source mounting part 232 including three PCBs is illustrated in FIGS. 2 to 3, the number of the PCBs is not limited thereto. Meanwhile, the PCB may be implemented as a flexible PCB (FPCB) with ductility.

The light guide mechanism 231 may be coupled fastened to the laser light source mounting part 232. In particular, the light guide mechanism 231 may be fastened to correspond to the position of the first laser light source mounted on the laser light source mounting part 232.

Since the laser light source mounting part 232 is inserted into the light guide part fastening groove 223 of the support part 22, the light guide part 23 may be fixed and supported by the support part 22.

A plurality of second laser light sources (laser diodes) and a plurality of LEDs are mounted in the care light source mounting part 24, and a circuit pattern for supplying power to the plurality of second laser light sources and the plurality of LEDs may be formed. For example, the plurality of second laser light sources and the plurality of LEDs may be disposed to irradiate light toward the lower portion of the care light source mounting part 24 (in the direction of the inner case 25).

In this regard, referring to FIG. 5, the care light source mounting part 24 may include a substrate 241. The substrate 241 may be implemented as a flexible FPCB with ductility. Accordingly, the care light source mounting part 24 may be bent in a dome (or arcuate) shape to correspond to the shapes of the outer case 21 and the inner case 25. The care light source mounting part 24 may be stably maintained in the bent state by being fixed and supported by the above-described support part 22.

Meanwhile, the substrate 241 may include a plurality of openings 243 respectively formed at positions corresponding to some of the plurality of light guide mechanisms 231. The area of the opening 243 may be equal to or larger than the area of the light guide mechanism 231. The light guide mechanism 231 may be disposed on the corresponding opening 243, or a portion including the lower surface may be disposed under the substrate 241 through the opening 243.

Accordingly, the laser light emitted from each of the plurality of light guide mechanisms 231 may be irradiated to the user's scalp through the opening 243 formed at the corresponding position.

Meanwhile, a plurality of branch substrates 242 may be formed at one corner of the substrate 241. The plurality of branch substrates 242 may extend from one corner of the substrate 241. In FIG. 5, an example in which the plurality of branch substrates 242 radially extend from one corner of the substrate 241 is illustrated, but this is not necessarily the case.

For example, the substrate 241 may have three corners in a rectangular shape, and the other corner may include two straight parts and a curved part formed between the two straight parts. The curved part may be convex in an outer direction of the substrate 241. The plurality of branch substrates 242 may each extend from the curved part.

The plurality of branch substrates 242 may be formed to be spaced apart from each other by a predetermined distance. In addition, the branch substrates 242 located at the edges may be formed so that one corner (for example, the straight part) of the substrate is also spaced apart by a predetermined distance. Accordingly, a plurality of gap regions 244 may be formed between the plurality of branch substrates 242 and between the branch substrate 242 and the substrate 241 positioned at the edges. The plurality of gap regions 244 may be formed to correspond to the light guide mechanisms 231 disposed in the relatively front of the plurality of light guide mechanisms 231. The light guide mechanism 231 may be disposed on the corresponding gap region 244, or a portion including the lower surface may be disposed under the substrate 241 through the gap region 244.

Accordingly, the laser light emitted from each of the light guide mechanisms 231 disposed in the front may be irradiated to the user's scalp through the gap regions 244.

Meanwhile, a plurality of second laser light sources 245 and LEDs 246 may be disposed on a bottom surface of the substrate 241 to be spaced apart from each other.

The output of the second laser light source 245 may be lower than that of the first laser light source 1000 (refer to FIG. 11) provided in the light guide part 23, but this is not necessarily the case. In addition, the output of the LEDs 246 may be lower than the output of each of the first laser light source 1000 and the second laser light source 245.

Meanwhile, the number of the first laser light sources 1000 may be less than the number of the second laser light sources 245, and the number of the second laser light sources 245 may be less than the number of the LEDs 246.

The laser light sources 1000 and 245 and the LED 246 may output red light. For example, the red light may correspond to a wavelength of about 630 nm to 670 nm, but this is not necessarily the case. According to an embodiment, the laser light sources 1000 and 245 and the LED 246 may output infrared light having a wavelength of about 780 nm to 1 mm.

Meanwhile, each of the second laser light sources 245 may include a photodiode 264 for sensing the amount of light. The light outputting device 1 may accurately detect the user's hair loss condition or hair loss type using the image sensor 262 and the plurality of photodiodes 264.

Further, on the substrate 241, a temperature/humidity sensor mounting region 247 in which a temperature/humidity sensor 266 (refer to FIG. 6) is mounted, and an image sensor mounting region 248 in which an image sensor 262 (refer to FIG. 6) is mounted may be formed. For example, each of the temperature/humidity sensor mounting region 247 and the image sensor mounting region 248 is formed closer to the center than the corner of the substrate 241, so that when the care main body 2 is worn, the user's parietal region (or crown region) can be located. Accordingly, the temperature/humidity sensor 266 can effectively detect heat or moisture generated from the user's head. In addition, the image sensor 262 may effectively obtain an image for detecting whether hair loss is present in the parietal region or the crown region.

Meanwhile, a sensor controller for controlling the care light source driver for driving the plurality of laser light sources and the plurality of LEDs, the image sensor 262, the temperature/humidity sensor 266, and the like may be implemented on a separate PCB provided inside or outside the care main body 2. According to an embodiment, the care light source driver and the sensor controller may be implemented in the care light source mounting part 24.

Referring to FIGS. 2 and 3, the inner case 25 may be formed on the innermost side of the care main body 2. The above-described support part 22, the light guide part 23, and the care light source mounting part 24 may be accommodated between the outer case 21 and the inner case 25 to be protected from the outside.

The inner case 25 may have a dome shape corresponding to the shape of the outer case 21. The inner case 25 may have a smaller size than the outer case 21, but this is not necessarily the case.

The inner case 25 is implemented with a material such as transparent plastic and silicone, and the light emitted from the laser light sources and LEDs accommodated therein can transmit through the inner case 25 and be irradiated to the user's scalp.

According to an embodiment, a plurality of light guide mechanism openings 252 corresponding to positions of the plurality of light guide mechanisms 23 may be formed in the inner case 25. The laser light emitted from the light guide part 23 may be irradiated to the user's scalp through the plurality of light guide mechanism openings 252.

In addition, in order to improve the sensing accuracy of the temperature/humidity sensor 266 and the image sensor 262, the inner case 25 has a temperature/humidity sensor opening 254 corresponding to the temperature/humidity sensor 266 and an image sensor opening 256 corresponding to the sensor 262 may be further formed.

Hereinafter, features related to the disposition of the light source and sensors of the care main body will be described in more detail with reference to FIGS. 6 to 7.

FIG. 6 is a bottom view illustrating a care main body of the light outputting device illustrated in FIG. 1. FIG. 7 is an enlarged view illustrating a laser light source, an image sensor, and a temperature/humidity sensor included in the care main body.

Referring to FIGS. 6 and 7, each of the plurality of light guide mechanisms 231 is exposed to the bottom surface of the care main body 2 through the opening 243 or the gap region 244 of the substrate 241 as described above, and the laser light can be irradiated to the user's scalp. In addition, in the inner case 25, the light guide mechanism openings 252 corresponding to the plurality of light guide mechanisms 231 are formed, so that It is possible to prevent the intensity of the laser light emitted from the light guide mechanism 231 from decreasing when the laser light transmits through the inner case 25.

In particular, the light guide mechanism 231 is implemented to distribute the laser light emitted from the first laser light source 1000 to irradiate the plurality of areas, and the interval between the plurality of areas is small compared to the distance between the second laser light sources 245. Accordingly, the light guide mechanism 231 can more densely irradiate the laser light to a specific area, thereby maximizing the care effect. In addition, the light guide mechanism 231 can maximize efficiency by irradiating laser light to a wide area with one first laser light source 1000.

Meanwhile, light emitted from the second laser light sources 245 and LEDs 246 may transmit through the inner case 25 and be irradiated to the user's scalp.

The plurality of LEDs 246 may be evenly distributed in various regions of the substrate 241 to provide an overall care function for various regions of the user's head.

According to an embodiment of the present disclosure, the light outputting device 1 may obtain the user's hair loss type information by using at least one image sensor 262a and 262b. For example, the first image sensor 262a may be disposed to face the forehead region of the user from the front side of the inner surface of the outer case 21. In addition, the second image sensor 262b may be disposed to face the user's parietal region and crown region from the center side of the light outputting device 1.

The light outputting device 1 may obtain the user's hair loss type information based on images (head images) obtained by the first image sensor 262a and the second image sensor 262b.

Meanwhile, a photodiode 264 for sensing the amount of light may be provided in each of the laser light sources 246 dispersedly disposed in the care main body.

The light outputting device 1 may detect a hair loss condition of each of the user's scalp regions by using the photodiodes 264 and may adjust the amount of light applied to each of the scalp regions based on the detection result.

Meanwhile, as the care light sources 1000, 245, and 246 emit light, the care light sources may emit heat together with the light. In this case, the performance of the care light sources 1000, 245, and 246 may gradually deteriorate due to the heat.

In addition, there is a fear that side effects may occur to the user as the user's scalp temperature rises or sweat occurs from the scalp due to the heat, and the light emitted from the care light sources 1000, 245, and 246 may be reflected by sweat generated on the scalp, thereby reducing the care effect.

The controller 550 may control the care light sources 1000, 245, and 246 to obtain temperature and humidity information through the temperature/humidity sensor 266 while irradiating light to the scalp and may control the care light sources 1000, 245, and 246 based on the obtained temperature and humidity information.

For example, the temperature/humidity sensor 266 may be provided to face the inside (scalp side) at a predetermined position of the light outputting device 1 to detect temperature and humidity. To this end, the temperature/humidity sensor 266 may include a temperature sensor 266a and a humidity sensor 266b. According to an embodiment, the temperature/humidity sensor 266 may further include a moisture content detection sensor 266c for directly detecting the moisture content present in the scalp or hair.

FIG. 8 is a block diagram illustrating a control configuration of a light outputting device for scalp care according to an embodiment of the present disclosure.

In FIG. 8, although it is assumed that the control components of the light outputting device 1 are dispersedly provided in the care main body 2 and the user manipulation device 5, according to an embodiment, all of the control components may be provided in the care main body 2.

Referring to FIG. 8, the care main body 2 of the light outputting device 1 may include a plurality of first laser light sources 1000, a plurality of second laser light sources 245, a plurality of LEDs 246, at least one image sensor 262, a temperature/humidity sensor 266, and a controller 270.

The plurality of first laser light sources 1000 and second laser light sources 245 may be implemented as laser diodes emitting laser light. As described above, the amount (output) of light of the first laser light source 1000 may be greater than that of the second laser light source 245. In addition, the number of the first laser light sources 1000 may be less than the number of the second laser light sources 245.

The plurality of first laser light sources 1000 may be provided to correspond to the plurality of light guide mechanisms 231 illustrated in FIG. 2. The plurality of first laser light sources 1000 may not be disposed to directly face the scalp when worn.

The plurality of second laser light sources 245 may be mounted to be spaced apart from each other in the care light source mounting part 24 as illustrated in FIGS. 5 to 6.

Meanwhile, as described above with reference to FIG. 10, the first laser light sources 1000 and the second laser light sources 245 may be disposed to correspond to a region including the forehead region 711, the frontal temporal regions 712 and 713, the parietal region 720, and the crown region 730.

The plurality of LEDs 246 may be disposed in various regions of the substrate 241 to irradiate light to various regions of the user's scalp.

Meanwhile, each of the first laser light sources 1000, the second laser light sources 245, and the plurality of LEDs 246 may emit red light having a wavelength of about 630 nm to 670 nm. Red light can promote hair growth by promoting the activity of hair follicles.

At least one image sensor 262 may obtain an image including the user's head region. The controller 550 may detect the user's hair loss condition, hair loss type, and the like, based on the obtained image. According to an embodiment, each of the second laser light sources 245 may include a photodiode 264. In this case, the controller 550 may detect the hair loss condition, the hair loss type, or the like using the at least one image sensor 262 and the photodiode 264.

The temperature/humidity sensor 266 may sense the temperature and humidity of a region adjacent to the user's scalp during the operation of the light outputting device 1. The controller 550 may control the light output of the care light sources 1000, 245, and 246 based on the sensed temperature and humidity.

The controller 270 provided in the care main body 2 may include a care light source driver 272 for controlling on/off of the care light sources 1000, 245, and 246 and a sensor controller 274 for controlling the operation of the sensors 262, 264, 266.

When a control signal for each of the care light sources 1000, 245, and 246 is received from the processor 552 of the controller 550, the care light source driver 272 can control each light output of the care light sources 1000, 245, and 246 based on the received control signal.

In addition, when a control signal for each of the sensors 262, 264, and 266 is received from the processor 552, the sensor controller 274 can control driving of the sensors 262, 264 and 266 based on the received control signal. The sensor controller 274 may transmit sensing data received from each of the sensors 262, 264, and 266 to the processor 552.

According to an embodiment, the care light source driver 272 and the sensor controller 274 may be implemented in the controller 550 or may be implemented integrally with the processor 552.

Meanwhile, the user manipulation device 5 of the light outputting device 1 includes a communication part 510, an input part 520, an output part 530, a memory 540, a controller 550, and a power supply part 560.

The communication part 510 may include at least one communication module for connecting the light outputting device 1 to a user's mobile terminal (smartphone, tablet PC, or the like), a server, or the like. For example, the at least one communication module may support a short-range wireless communication method such as Bluetooth or support a wireless Internet method such as Wi-Fi.

For example, the controller 550 may transmit operation or condition information of the light outputting device 1 to the user's mobile terminal through the communication part 510. Also, the controller 350 may transmit the user's scalp condition information, hair loss condition information, and/or hair loss type information to the user's mobile terminal through the communication part 510. The scalp condition information, hair loss condition information, and hair loss type information may be information obtained based on sensing data of the image sensor 262 and/or the plurality of photodiodes 264.

The input part 520 may receive an input related to power on/off of the light outputting device 1, setting of an operation mode, and the like, from a user. For example, the input part 520 may include at least one button.

The output part 530 may output information such as a power condition, an operation mode, and a battery condition of the light outputting device 1. For example, the output part 530 may include at least one light source 532 and a speaker 534 that outputs the information in the form of sound.

The memory 540 may include control data for controlling components included in the light outputting device 1 or data related to light output setting of the care light sources 1000, 245, and 246 according to each of a plurality of operation modes.

In addition, the memory 540 may include data or algorithms for generating scalp condition information, hair loss condition information, and/or hair loss type information from sensing values provided from the image sensor 262 and/or the plurality of photodiodes 264.

In addition, the memory 540 may include data or an algorithm for controlling the light output of the care light sources 1000, 245, and 246 based on temperature and humidity information provided from the temperature/humidity sensor 266.

The memory 540 may be understood as a concept encompassing at least one volatile memory (RAM, or the like) and at least one non-volatile memory (ROM, Flash memory, or the like).

The controller 550 may control the overall operation of the light outputting device 1. The controller 550 may include at least one processor (or controller). In addition, in terms of hardware, the controller 550 may include at least one CPU, an application processor (AP), a microcomputer, an IC, an application specific integrated circuit (ASIC), and the like.

For example, the controller 550 may include a processor (main processor) 552, an image signal processor (ISP) 554, an amplifier IC 556, a charger IC 558, and the like.

The processor 552 may correspond to a main processor that controls the overall operation of the light outputting device 1. For example, the processor 552 may set an operation mode of the light outputting device 1 based on an input received through the input part 520 and control components included in the light outputting device 1 according to the set operation mode. In addition, the processor 552 can control the operations of the other components 554, 556, and 558 included in the controller 550, and even the operations of the care light source driver 272 and the sensor controller 274 of the care main body 2.

Meanwhile, the processor 552 may detect a hair loss condition or a hair loss type of the user based on sensing values obtained from the image sensor 262 and/or the plurality of photodiodes 264. The processor 552 can control the light output of the care light sources 1000, 245, and 246 corresponding to at least one of the plurality of zones (ZONE1 to ZONE3; see FIG. 7) based on the detected hair loss condition or hair loss type.

The ISP 554 may generate an image by processing the sensing value obtained from the image sensor 262. The generated image may include the user's scalp. The processor 552 may transmit the generated image to the user's terminal or the like through the communication part 510.

The amplifier IC 556 may control the sound output of the speaker 534 included in the output part 530, and the charger IC 558 may charge or control supply power to the battery 562 of the power supply part 560.

The power supply part 560 may provide power required for the operation of the light outputting device 1 to each of the components. For example, the power supply part 560 may include a battery 562. The power supply part 560 may include a terminal for connecting to an external power supply source and may charge the battery 562 with power supplied from the outside through the terminal. The power supply part 560 may supply power to components included in the care main body 2 through the cable 52.

Hereinafter, embodiments related to the control operation of the light outputting device 1 will be described with reference to FIGS. 9 to 16.

FIG. 9 is a flowchart illustrating a method for controlling a light outputting device for scalp care according to an embodiment of the present disclosure. FIG. 10 is an exemplary view related to an operation of determining a care light source to be activated based on the user's hair loss type described in FIG. 9.

Referring to FIG. 9, the processor 552 may obtain a head image of the wearer (user) using at least one image sensor 262 (S100).

For example, in a case where the light outputting device 1 is first driven or in a case where a request for measurement of a hair loss type is received from a user through the input part 520, the processor 552 uses the at least one image sensor 262 to obtain a head image of the user.

As described above in FIG. 6, in a case where the at least one image sensor 262 includes the first image sensor 262a and the second image sensor 262b, the head image may include a first head image obtained from the first image sensor 262a and a second head image obtained from the second image sensor 262b. For example, the first head image may include the user's forehead region, and the second head image may include the user's crown region and parietal region.

The light outputting device 1 may obtain information on the user's hair loss type based on the obtained head image (S110). The light outputting device 1 may determine the care light sources to be activated (driven) among the plurality of care light sources 1000, 245, and 246 included in the light outputting device 1 based on the obtained hair loss type information. (S120).

Referring to FIG. 10 in relation to steps S110 and S120, the hair loss of the person 700 may mainly occur in the forehead region 711, the frontal temporal regions 712 and 713, the parietal region 720, and the crown region 730.

Accordingly, according to an embodiment of the present disclosure, the plurality of light guide mechanisms 231 and the second laser light sources 245 emitting laser light are disposed to correspond to the forehead region 711, the frontal temporal regions 712 and 713, the parietal region 720, and the crown region 730 to provide a more intensive care function for the regions.

On the other hand, in general, since hair loss is relatively low in the temporal region, the light guide mechanism 231 and the second laser light source 245 are not disposed at positions corresponding to the temporal region, thereby providing an efficient care function, but, the present disclosure is not limited thereto.

The processor 552 may obtain the user's hair loss type information based on the obtained head image.

When dividing the general hair loss types, there are M-type hair loss in which hair loss gradually progresses from the frontal temporal regions 712 and 713, V-type hair loss in which hair loss gradually progresses from the crown region 730, F-type hair loss in which hair loss gradually progresses from the parietal region 720, U-type hair loss in which hair loss complexly progresses in the frontal region 711, the frontal temporal region 712, 713, the parietal region 720, and the crown region 730.

The processor 552 can obtain information of the type of hair loss based on the color, brightness, or the like of the region corresponding to each of the frontal region 711, the frontal temporal region 712, 713, the parietal region 720, and the crown region 730 from the obtained head image.

Meanwhile, the light outputting device 1 according to the embodiment of the present disclosure can partition laser light sources (1000, 245), and LEDs (246) provided in the care main body (2) into a plurality of zones (for example, ZONE1, ZONE2, Zone3).

The light outputting device 1 may drive the laser light sources 1000 and 245 and/or the LEDs 246 included in at least one zone based on the obtained hair loss type information.

For example, when the detected hair loss type is M-type hair loss, the processor 552 turns on only the laser light sources corresponding to the first zone ZONE1, and may not turn on the laser light sources corresponding to the second zone ZONE2 and the third zone ZONE3. Similarly, the controller 550 may turn on only the LEDs corresponding to the first zone ZONE1 and may not turn on the LEDs corresponding to the remaining zones. However, in order to provide an overall care function for the entire scalp according to an embodiment, the controller 550 may turn on all of the LEDs regardless of the hair loss type.

According to an embodiment, the processor 552 may transmit the obtained head image to an electronic device such as a server through the communication part 510. The server may obtain the user's hair loss type information by analyzing the received head image and transmit the obtained hair loss type information to the light outputting device 1.

FIG. 9 will be described again.

The light outputting device 1 may set the light amount of the care light sources to be driven based on the light amount measurement result of the photodiodes 264 included in the second laser light sources 245 (S130). The light outputting device 1 may perform a scalp care operation by driving the care light sources based on the set amount of light (S140).

In other words, care light sources to be driven may be determined based on steps S110 to S120, and a light amount of each of the care light sources to be driven may be individually set based on steps S130 to S140.

Steps S130 to S140 will be described in more detail later with reference to FIGS. 11 to 14.

The light outputting device 1 may adjust the amount of light or stop the scalp care operation based on the measurement result of the temperature/humidity sensor 266 while the care light source is being driven (S150).

The processor 552 may minimize the occurrence of side effects and may minimize the performance of the light outputting device 1 by adjusting the amount of light of the care light source or stopping the scalp care operation based on the change in scalp temperature or humidity while the care light source is being driven.

An embodiment related to step S150 will be described with reference to FIGS. 15 to 16.

FIG. 11 is a flowchart illustrating an embodiment of an operation of setting a light amount of a care light source based on a light amount sensing value of photodiodes included in laser light sources. FIG. 12 is an exemplary view related to the embodiment of FIG. 11.

Referring to FIG. 11, the light outputting device 1 may turn on the LEDs 246 among the care light sources and turn off the second laser light sources 245 (S200).

The light outputting device 1 can obtain a light amount sensing value of each of the photodiodes 264 included in the second laser light sources 245 (S210) and, based on the obtained light amount sensing value, set the light amount of each of the care light sources 1000, 245 and 246 (S220).

The light outputting device 1 may drive the care light sources 1000, 245, and 246 based on the set amount of light (S230).

In this regard, referring to FIG. 12, the processor 552 may turn on the LEDs 246a and 246b and turn off the second laser light source 245a.

In this case, the photodiode 264a provided in the second laser light source 245a may sense the amount of light emitted from the LEDs 246a and 246b and reflected from the scalp.

The amount of light sensed by the photodiode 264a may be related to the progress of hair loss in the scalp region corresponding to the second laser light source 245a. For example, as the hair loss progress of the corresponding scalp region increases, the amount of light sensed by the photodiode 264a may increase.

The processor 552 may receive the light amount sensing value of the photodiode 264a and may set the amount of light of the second laser light source 245a and the care light sources 1000, 245, and 246 which is present in a predetermined area including the second laser light source 245a based on the received light amount sensing value.

For example, the processor 552 may increase the amount of light of the care light sources 1000, 245, and 246 as the received light amount sensing value is higher. On the other hand, as the received light amount sensing value is lower, the processor 552 may decrease the light amount of the care light sources 1000, 245, and 246.

For example, in a case where the light amount sensing value is the first sensing value, the processor 552 may set the light amount of the care light sources 1000, 245, and 246 existing in the predetermined area as the first light amount. On the other hand, in a case where the light amount sensing value is a second sensing value higher than the first sensing value, the processor 552 may set the light amount of the care light sources 1000, 245, and 246 to a second light amount equal to or greater than the first light amount.

FIG. 13 is a flowchart for explaining an embodiment of an operation of setting a light amount of a care light source based on a light amount sensing value of photodiodes included in laser light sources. FIG. 14 is an exemplary view related to the embodiment of FIG. 13.

Referring to FIGS. 13 to 14, the light outputting device 1 may turn off any one 245a of the plurality of second laser light sources 245 and turn on at least one second laser light source 245b to 245g around the second laser light sources 245a (S300).

At least one second laser light source 245b to 245g around the turned-off second laser light source 245a may mean a second laser light source disposed within a preset distance from the turned-off second laser light source 245a.

The light outputting device 1 may obtain a light amount sensing value from the photodiode 264a included in the turned-off second laser light source 245a (S310).

Similarly to that described above in FIGS. 11 to 12, the photodiode 264a can detect the amount of light emitted from at least one second laser light source 245b to 245g around the turned off second laser light source 245a and reflected from the scalp.

For example, the processor 552 can sequentially obtain the light amount sensing values through the photodiode 264a while sequentially turning on at least one second laser light source 245b to 245g around the turned-off second laser light source 245a one by one. The processor 552 may calculate the average value of the sequentially obtained light amount sensing values to set the light amount of the care light sources.

As another example, the processor 552 may obtain a light amount sensing value through the photodiode 264a while turning on some of the at least one second laser light source 245b to 245g in combination.

As another example, the processor 552 may obtain a light amount sensing value through the photodiode 264a while turning on all of the at least one second laser light source 245b to 245g.

The amount of light sensed by the photodiode 264a may be related to the degree of hair loss in the scalp region corresponding to the turned-off second laser light source 245a. For example, as the hair loss progress of the corresponding scalp region increases, the amount of light sensed by the photodiode 264a may increase.

The light outputting device 1 may set the light amount of the care light sources 1000, 245, and 246 in a predetermined region including the second laser light source 245a based on the obtained light amount sensing value (S320). The light outputting device 1 may drive the care light sources 1000, 245, and 246 based on the set amount of light (S330).

According to embodiments of FIGS. 11 to 14, the processor 552 may obtain a light amount sensing value of the photodiodes 264 included in the plurality of second laser light sources 245, respectively. The processor 552 may set different light amounts of each of the care light sources 1000, 245, and 246 based on the obtained light amount sensing values.

Accordingly, the light outputting device 1 may provide an efficient scalp care function by differently setting the amount of light according to the hair loss progress of each of the scalp regions.

FIG. 15 is a flowchart for explaining an operation in which the light outputting device for scalp care adjusts the operation of the care light source according to the temperature change detected through the temperature/humidity sensor while the care light source is being driven.

Referring to FIG. 15, the light outputting device 1 may periodically obtain a temperature sensing value through the temperature/humidity sensor 266 while the care light sources 1000, 245, and 246 are being driven (S400).

When the care light sources 1000, 245, and 246 are turned on as the light outputting device 1 performs a scalp care function, the temperature of the scalp and of the region around the scalp can increase by heat generated from the care light sources 1000, 245, and 246.

In a case where the temperature of the scalp and of the region around the scalp increases excessively, the light output efficiency of the care light sources 1000, 245, and 246 may decrease, and thus the performance of the light outputting device 1 may be deteriorated. In addition, in the case of a user having sensitive skin characteristics, side effects such as worsening of the scalp condition may occur as the scalp temperature increases.

The light outputting device 1 may check the scalp temperature increasing amount during scalp care based on the currently obtained temperature sensing value and the initially obtained temperature sensing value (S410).

The processor 552 may check the scalp temperature increasing amount during scalp care based on a difference between the scalp temperature when the care light sources 1000, 245, and 246 are turned on and the current scalp temperature. This is because the scalp temperature of each user may be different from each other.

In a case where the checked scalp temperature increase amount is equal to or greater than the threshold value (YES in S420), the light outputting device 1 may decrease the light amount of the activated care light sources 1000, 245, 246 or stop the driving of the care light sources 1000, 245, 246 (S430).

The processor 552 may reduce the amount of light of the activated care light sources 1000, 245, and 246 by a predetermined amount in a case where the scalp temperature increasing amount is equal to or greater than a threshold (for example, 2° C.).

Even after a predetermined period of time has elapsed after the decrease in the amount of light, in a case where the scalp temperature increasing amount is maintained the threshold value or more, the processor 552 may turn off the care light sources 1000, 245, and 246.

According to an embodiment, the processor 552 may output a message inducing the user to reuse the light outputting device 1 after a break for a predetermined time through the output part 530.

FIG. 16 is a flowchart for explaining an operation in which the light outputting device for scalp care adjusts the operation of the care light source according to the humidity change detected through the temperature/humidity sensor while the care light source is being driven.

Referring to FIG. 16, the light outputting device 1 may periodically obtain a humidity sensing value through the temperature/humidity sensor 266 while the care light sources 1000, 245, and 246 are being driven (S500).

When the care light sources 1000, 245, and 246 are turned on as the light outputting device 1 performs a scalp care function, the temperature of the scalp and of the region around the scalp can increase by heat generated from the care light sources 1000, 245, and 246. In a case where the temperature of the scalp and of the region around the scalp increases, the humidity of the scalp and of the region around the scalp may increase as sweat is generated from the scalp.

When sweat occurs on the scalp, the scalp care effect may be deteriorated as the light emitted from the care light sources 1000, 245, and 246 is not sufficiently irradiated to the scalp. In addition, in a case where the humidity of the scalp and of the region around the scalp increase, as moisture is generated in the care light sources 1000, 245, 246, the circuit of the light outputting device 1, or the like, performance degradation or damage to the light outputting device 1 may occur.

Meanwhile, according to an embodiment, the user may wear the light outputting device 1 with hair wet. To prevent the light outputting device 1 from being used with hair wet, the processor 552 may induce the light outputting device 1 to be reused (such as outputting a message through the output part 530) after the hair is dried in a case where the initially obtained humidity sensing value is equal to or greater than the reference value.

The light outputting device 1 may check the humidity change amount based on the obtained humidity sensing value (S510).

At a point in time when sweat is generated from the user's scalp during scalp care, the humidity of the scalp and of the region around the scalp may rapidly increase. Accordingly, the processor 552 may check the humidity change amount based on the difference between the previously obtained humidity sensing value and the currently obtained humidity sensing value.

When the checked humidity change amount (increase amount) is equal to or greater than the threshold (YES in S520), the light outputting device 1 may stop driving the activated care light sources 1000, 245, and 246 (S530).

The processor 552 may recognize that sweat is generated from the scalp in a case where the humidity change amount is greater than or equal to a threshold value. Accordingly, the processor 552 may turn off the activated care light sources 1000, 245, and 246.

According to an embodiment, the processor 552 may output a message inducing the user to reuse the light outputting device 1 after a break for a predetermined time through the output part 530.

In other words, according to the embodiment illustrated in FIGS. 13 to 16, the light outputting device 1 can actively adjust the amount of light or drive of the care light source according to the user's scalp condition (temperature, humidity, or the like) while driving the care light source according to the performance of the scalp care function. Accordingly, deterioration or damage to the performance of the light outputting device 1 may be prevented, and the risk of deterioration of the user's scalp condition may be prevented in advance.

The above description is merely illustrative of the technical spirit of the present disclosure, and various modifications and variations will be possible without departing from the essential characteristics of the present disclosure by those skilled in the art to which the present disclosure pertains.

Therefore, the embodiments disclosed in the present disclosure are not intended to limit the technical spirit of the present disclosure, but to explain, and the scope of the technical spirit of the present disclosure is not limited by these embodiments.

The protection scope of the present disclosure should be construed by the following claims, and all technical ideas within the scope equivalent thereto should be construed as being included in the scope of the present disclosure.

The invention claimed is:

1. A light outputting device for scalp care comprising:
   an outer case having a dome shape to form an outer appearance;
   an inner case located at an inside of the outer case;
   a plurality of laser light sources disposed in a space between the outer case and the inner case;
   a plurality of photodiodes comprising a respective photodiode located at each of the plurality of laser light sources; and
   a processor configured to:
   obtain a light amount sensing value of a first photodiode among the plurality of photodiodes,
   set a light amount for a first laser light source corresponding to the first photodiode based on the obtained light amount sensing value, and
   drive the first laser light source based on the set light amount,
   wherein the processor is further configured to:
   turn on at least one laser light source disposed within a predetermined distance from the first laser light source among the plurality of laser light sources, and
   obtain the light amount sensing value of the first photodiode based on light emitted when the at least one laser light source is turned on, and
   wherein the processor is further configured to:
   sequentially turn on the at least one laser light source and sequentially obtain at least one light amount sensing value through the first photodiode, and
   determine an average value of at least one sequentially obtained light amount sensing value, wherein the light amount for the first laser light source is set based on the determined average value.

2. The light outputting device for scalp care of claim 1, wherein the light amount for the first laser light source is set to a first light amount based on the light amount sensing value being equal to a first sensing value, and
   wherein the light amount for the first laser light source is set to a second light amount equal to or greater than the first light amount based on the light amount sensing value being equal to a second sensing value higher than the first sensing value.

3. The light outputting device for scalp care of claim 1, further comprising:
   a plurality of light emitting diodes (LEDs) disposed in the space between the outer case and the inner case,
   wherein the processor is further configured to set a light amount for at least one LED within a predetermined distance from the first laser light source based on the light amount sensing value of the first photodiode.

4. The light outputting device for scalp care of claim 3, wherein the processor is further configured to:
   turn on the at least one LED among the plurality of LEDs, and obtain the light amount sensing value of the first photodiode based on light emitted when the at least one LED is turned on.

5. The light outputting device for scalp care of claim 1, further comprising:
a temperature sensor,
wherein the processor is further configured to:
obtain a temperature sensing value through the temperature sensor while driving at least one of the plurality of laser light sources, and
adjust the light amount of the first laser light source during the driving or stop the driving of the first laser light source based on the obtained temperature sensing value.

6. A light outputting device for scalp care comprising:
an outer case having a dome shape to form an outer appearance;
an inner case located at an inside of the outer case;
a plurality of laser light sources disposed in a space between the outer case and the inner case;
a plurality of photodiodes comprising a respective photodiode located at each of the plurality of laser light sources; and
a processor configured to:
obtain a light amount sensing value of a first photodiode among the plurality of photodiodes,
set a light amount for a first laser light source corresponding to the first photodiode based on the obtained light amount sensing value, and
drive the first laser light source based on the set light amount; and
a temperature sensor,
wherein the processor is further configured to:
obtain a temperature sensing value through the temperature sensor while driving at least one of the plurality of laser light sources, and
adjust the light amount of the at least one laser light source during the driving or stop the driving of the at least one laser light source based on the obtained temperature sensing value,
wherein the processor is further configured to:
determine an amount of increase in scalp temperature based on a difference between an initial temperature sensing value and the obtained temperature sensing value and
reduce the light amount from the first laser light based on the determined amount of increase in scalp temperature being higher than a threshold value.

7. The light outputting device for scalp care of claim 6, wherein the processor is further configured to:
obtain a temperature sensing value through the temperature sensor after a predetermined time has elapsed from a time when the amount of light of the first laser light source is reduced,
determine the amount of increase in scalp temperature based on the difference between the initial temperature sensing value and the obtained temperature sensing value, and
stop the driving of the first laser light source based on the determined amount of increase in scalp temperature being maintained at an amount higher than the threshold value.

8. The light outputting device for scalp care of claim 1, further comprising:
a humidity sensor,
wherein the processor is further configured to:
periodically obtain a humidity sensing value through the humidity sensor while driving at least one of the plurality of laser light sources, and
stop the driving of the first laser light source during the driving according to a humidity change amount determined based on the periodically obtained humidity sensing value.

9. The light outputting device for scalp care of claim 1, further comprising:
at least one image sensor disposed to capture an interior of the light outputting device for scalp care,
wherein the processor is further configured to:
obtain a head image including a scalp of a user of the light outputting device through the at least one image sensor,
obtain hair loss type information of the user based on the obtained head image, and
select at least one laser light source to be driven among the plurality of laser light sources based on the obtained hair loss type information.

10. The light outputting device for scalp care of claim 9, further comprising:
a transceiver configured to connect with a server or an electronic device,
wherein the processor is further configured to:
control a communication part to transmit the obtained head image to the server or the electronic device and
receive, from the server or the electronic device, the hair loss type information based on the obtained head image.

11. A method for controlling a light outputting device for scalp care including a plurality of laser light sources, and a plurality of photodiodes comprising a respective photodiode located at each of the plurality of laser light sources, the method comprising:
obtaining a light amount sensing value of a first photodiode among the plurality of photodiodes;
setting a light amount for a first laser light source corresponding to the first photodiode based on the obtained light amount sensing value;
driving the first laser light source based on the set light amount;
obtaining a humidity sensing value through a humidity sensor while driving at least one of the plurality of laser light sources, and
stopping the driving of the first laser light source during the driving based on the obtained humidity sensing value.

12. The method for controlling a light outputting device for scalp care of claim 11,
wherein the light amount for the first laser light source is set to a first light amount based on the light amount sensing value being equal to a first sensing value, and
wherein the light amount for the first laser light source is set to a second light amount equal to or greater than the first light amount based on the light amount sensing value being equal to a second sensing value higher than the first sensing value.

13. The method for controlling a light outputting device for scalp care of claim 11, further comprising:
turning on at least one laser light source disposed within a predetermined distance from the first laser light source among the plurality of laser light sources, and obtaining the light amount sensing value of the first photodiode based on light emitted when the at least one laser light source is turned on.

14. The method for controlling a light outputting device for scalp care of claim 11,
wherein the light outputting device for scalp care further includes a plurality of light emitting diodes (LEDs),
wherein the method further comprises setting a light amount for at least one LED within a predetermined distance from the first laser light source based on the light amount sensing value of the first photodiode.

15. The method for controlling a light outputting device for scalp care of claim 14, further comprising:
turning on at least one LED among the plurality of LEDs; and
obtaining the light amount sensing value of the first photodiode based on the light emitted when the at least one LED is turned on.

16. The method for controlling a light outputting device for scalp care of claim 11, further comprising:
obtaining a temperature sensing value through a temperature sensor while driving at least one of the plurality of laser light sources, and
adjusting the light amount of the first laser light source during the driving or stopping the driving of the first laser light source based on the obtained temperature sensing value.

17. The method for controlling a light outputting device for scalp care of claim 11, further comprising:
obtaining a head image including a scalp of a user of the light outputting device through at least one image sensor,
obtaining hair loss type information of the user based on the obtained head image, and
selecting at least one laser light source to be driven among the plurality of laser light sources based on the obtained hair loss type information.

* * * * *